United States Patent
Oda et al.

(10) Patent No.: US 6,630,215 B1
(45) Date of Patent: Oct. 7, 2003

(54) MEDICAL DEVICE

(75) Inventors: Takeshi Oda, Tokyo (JP); Yukiko Nishitoba, Tokyo (JP); Toru Arai, Tokyo (JP); Akio Okamoto, Tokyo (JP); Toshiaki Otsu, Tokyo (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/622,914

(22) PCT Filed: Mar. 8, 1999

(86) PCT No.: PCT/JP99/01105
§ 371 (c)(1),
(2), (4) Date: Sep. 7, 2000

(87) PCT Pub. No.: WO99/45980

PCT Pub. Date: Sep. 16, 1999

(30) Foreign Application Priority Data

Mar. 9, 1998 (JP) .......................................... 10-056876
Nov. 25, 1998 (JP) .......................................... 10-333990

(51) Int. Cl.⁷ .......................... A61J 1/10; A61L 15/24; A61L 29/04; C08K 5/01

(52) U.S. Cl. ...................... 428/35.7; 128/897; 602/904; 604/264; 604/404; 604/408; 604/910; 604/915; 428/36.8; 428/36.9; 428/36.92

(58) Field of Search ............................... 428/35.7, 36.8, 428/36.9, 36.92; 128/897; 602/904; 604/404, 408, 910, 915

(56) References Cited

U.S. PATENT DOCUMENTS

| 5,658,625 | A | * | 8/1997 | Bradfute et al. ............ 428/34.9 |
| 5,739,200 | A | * | 4/1998 | Cheung et al. .............. 524/504 |
| 5,865,814 | A | * | 2/1999 | Tuch ........................... 604/265 |
| 5,866,704 | A | * | 2/1999 | Nickias et al. ................ 556/11 |
| 6,194,501 | B1 | * | 2/2001 | Okada et al. ............... 524/274 |

FOREIGN PATENT DOCUMENTS

| DE | 19719593 A1 | * | 1/1999 |
| JP | 07179847 A | * | 7/1995 |

* cited by examiner

*Primary Examiner*—Sandra M. Nolan
(74) *Attorney, Agent, or Firm*—Oblon, Spivak, McClelland, Maier & Neustadt, P.C.

(57) ABSTRACT

A medical material and a medical device comprising an aromatic vinyl compound/α-olefin random copolymer according to the present invention, are materials which contain substantially no chlorine and which have not only excellent flexibility, transparency and proper resilience but also radiation resistance and biocompatibility, and they are hence advantageously used especially in the medical field.

8 Claims, No Drawings

MEDICAL DEVICE

TECHNICAL FIELD

The present invention relates to a medical material comprising an aromatic vinyl compound/α-olefin random copolymer and a medical device formed therefrom. More particularly, the present invention relates to a medical material which has not only radiation resistance but also biocompatibility, particularly blood compatibility and is excellent in the mechanical properties and transparency and which contains substantially no chlorine, and a medical device made thereof.

BACKGROUND ART

Medical devices such as tubes to be used for intravenous drip injection, catheters, circuits and bags or containers for bloods, infusion solutions and dialysis, are usually required to be excellent in not only flexibility, elasticity and transparency but also radiation resistance and biocompatibility, particularly blood compatibility. Further, sufficient strength durable for operations is also required. Especially, tubes are required to have proper elastic elongation and touchiness and to have so-called resilience. Heretofore, they have been produced in many cases from a soft vinyl chloride which is a base material having these properties. Further, in recent years, disposability of the medical devices has been advanced, and they are in many cases disposed by incineration treatment to prevent biohazard. With respect to medical devices wherein soft polyvinyl chloride is used, the load to the environment due to e.g. incineration is considered to be problematic, and a study is being made to substitute other materials for the soft polyvinyl chloride as the base material for medical devices.

As films and tubes containing no chlorine, those made of a linear low density ethylene/α-olefin type copolymer, have been known, but there has been no medical material which fully satisfies the above conditions as a medical material. As a resin composition which is excellent in flexibility and which presents a formed product suitable for medical use, JP-A-4-159344 proposes a resin composition comprising an olefin type resin, a hydrogenation product of styrene/butadiene block copolymer and a hydrogenation product of styrene/isoprene block copolymer. This resin composition presents a formed product which is excellent in flexibility and has a feature that even if the formed product is incinerated, no toxic gas will be formed. However, the formed product obtained by such a resin composition is not yet adequate in another property i.e. transparency required for medical devices and still has a room for improvement in this respect.

Further, JP-A-3-202298 discloses that a non-soft vinyl chloride resin, specifically a composition comprising a styrene type elastomer, polypropylene, etc. or a composition of a citric acid ester, has an activity to inhibit hemolysis, and JP-A-6-319785 discloses a thermoplastic polyester type composition. However, either one is not adequate as compared with the hemolysis inhibitory action of a plasticizer in the soft vinyl chloride resin and is poor in the practical applicability.

Further, among catheters, a balloon catheter of a type whereby a balloon is expanded in a blood vessel and then shrinked to be retained for a few days, has a problem such that if the surface loosens, a blood clot is likely to result due to slackening of blood flow. A gastrointestinal catheter is repeatedly pulled by a peristaltic motion of the gastrointestinal tract. Accordingly, in such an application, it is required to be excellent in strain recovery. Thermoplastic polyurethane used for conventional catheters is excellent in mechanical properties, but has a drawback that it is poor in strain recovery.

DISCLOSURE OF THE INVENTION

An object of the present invention is to provide a medical product which is excellent not only in flexibility, elasticity and transparency required for medical use but also in radiation resistance and biocompatibility including blood compatibility and which is free from generation a toxic gas at the time of incineration, and a medical device made thereof.

The present inventors have conducted an extensive study to solve the above problem and as a result, have found that an aromatic vinyl/α-olefin random copolymer or a resin composition having a plasticizer blended to such a copolymer in a certain amount, is suitable as a medical material or a material for a medical device, and have finally completed the present invention.

Namely, the present invention is a medical material and a medical device comprising an aromatic vinyl compound/α-olefin random copolymer, preferably a medical material and a medical device, obtained by processing a resin composition (C) comprising 100 parts by weight of a resin component (A) containing at least 50 wt % of an aromatic vinyl compound/α-olefin random copolymer and from 0.1 to 200 parts by weight, preferably from 0.5 to 100 parts by weight, more preferably from 1 to 50 parts by weight, of a plasticizer (B).

The medical material and the medical device of the present invention are excellent in flexibility, elasticity, transparency, radiation resistance and biocompatibility. In the present invention, a medical device is meant for a medical device to which sterilization treatment has been applied and which is to be used for medical application. A medical material is meant for a material for a medical device and is meant for e.g. a sheet (including a film and a plate) obtained by processing an aromatic vinyl compound/α-olefin random copolymer or its composition (C) by e.g. extrusion stretch forming.

The aromatic vinyl compound/α-olefin random copolymer to be used in the present invention, is basically a copolymer made of an aromatic vinyl compound monomer and an α-olefin monomer. The structure is not particularly limited. However, for example, an aromatic vinyl compound/α-olefin random copolymer obtainable by means of a metallocene catalyst of the chemical formula 1 which will be described hereinafter, has high stereo regularity and a head-to-tail chain structure of at least two aromatic vinyl compound units, whereby it is excellent in initial tensile modulus of elasticity, breaking strength, elongation, transparency and chemical resistance.

As the aromatic vinyl/α-olefin random copolymer to be used in the present invention, one having a weight average molecular weight of at least 30,000, is practical.

The upper limit for the weight average molecular weight is not particularly limited, but it is preferably at most 3,000,000, more preferably at most 1,000,000. If the molecular weight exceeds 3,000,000, the melt viscosity tends to increase, whereby molding by a common molding method such as injection molding or extrusion molding tends to be difficult.

Here, the weight average molecular weight (Mw) is a molecular weight calculated as polystyrene, obtained by GPC using standard polystyrene.

Further, the molecular weight distribution (Mw/Mn) is at most 6, preferably at most 4, particularly preferably at most 3. The molecular weight distribution being small or the uniformity of the resin being high consequently contributes to good transparency of the resin.

Mn represents a number average molecular weight and can likewise be measured by a GPC method.

With the aromatic vinyl compound/α-olefin random copolymer to be used in the present invention, the glass transition point (Tg) can be changed within a wide range depending upon the content of the aromatic vinyl compound. For example, with the styrene-ethylene random copolymer, Tg becomes to be close to 30° C. at a styrene content of 50% by molar ratio. Further, by using it in combination with a thermoplastic resin having Tg of at least 30° C, Tg as the composition can be set within a wide range, whereby the temperature dependency of viscoelasticity such as storage modulus or loss tangent (tanδ) can be controlled. Accordingly, in the present invention, Tg can be increased to a level close to normal temperature, if desired, by mixing a petroleum resin, a terpene resin, a cumarone-indene resin, a rosin type resin or hydrogenation derivatives thereof, having high Tg, to the aromatic vinyl compound/α-olefin random copolymer, whereby it becomes easy to accomplish specific viscoelastic properties.

Especially, with a catheter to be percutaneously inserted into the body, one having Tg of from 30 to 35° C. will be flexible in the body by the body temperature, whereby there is a merit that the possibility of damaging a human body system can be minimized.

Here, the thermoplastic resin having a glass transition temperature (Tg) of at least 30° C. may, for example, be a petroleum resin from cyclopentadiene or its dimer or an aromatic petroleum resin from a $C_9$ component; the terpene resin may, for example, be a terpene resin from β-pinene, or a terpene/phenol resin; and the rosin type resin may, for example, be a rosin resin such as gum rosin or wood rosin, or an esterified rosin resin modified by glycerol or pentaerythritol.

These includes ones having various Tg depending upon the molecular weights. However, those having a Tg of from 30 to 100° C., preferably from 70 to 90° C., are preferred. With one having a Tg of lower than 30° C., it will be necessary to mix it in a large amount in order to increase Tg depending upon the aromatic vinyl compound/α-olefin random copolymer to be mixed, whereby bleeding on the surface of the medical device is likely to be brought about, and a problem may result in the mechanical strength.

The method for preparing the aromatic vinyl compound/α-olefin random copolymer to be used in the present invention, is not particularly limited. However, a method of copolymerizing an aromatic vinyl compound and an α-olefin in the presence of a coordination polymerization catalyst, is a preferred method for preparation.

The coordination polymerization catalyst to be used, may be a soluble Zieglar-Natta catalyst or a transition metal compound catalyst activated by methyl aluminoxane or a boron compound (so-called metallocene catalyst or half metallocene catalyst, or CGCT catalyst).

Specifically, the polymerization catalysts disclosed in the following literatures and patents can be employed.

Metallocene catalysts are disclosed in U.S. Pat. No. 5,324,800, WO98/09999, JP-B-7-37488, JP-A-6-49132, Polymer Preprints, Japan, 42, 2292 (1993), Makromol. Chem., Rapid Commun., 17, 745 (1996) by the present inventors, JP-A-9-309925 and EP-0872492A2.

Half metallocene catalysts are disclosed in Makromol. Chem., 191, 2387 (1990).

GCCT catalysts are disclosed in JP-A-3-163088, JP-A-7-53618, and European Patent 416815.

The aromatic vinyl compound/α-olefin random copolymer to be used in the present invention includes, for example, an aromatic vinyl compound/α-olefin random copolymer obtained by means of the following transition metal compound or by the following production method. However, it is not limited by the transition metal compound or the production method of the present invention.

The aromatic vinyl compound/α-olefin random copolymer to be suitably used in the present invention, can be produced from an aromatic vinyl compound and an α-olefin by means of a catalyst comprising a transition metal compound of the following chemical formula 1 and a co-catalyst:

(Chemical Formula 1)

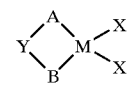

(wherein A and B are groups selected from an unsubstituted or substituted cyclopentaphenanthryl group (the following chemical formulae 2 to 3), an unsubstituted or substituted benzindenyl group (chemical formulae 4 to 6), an unsubstituted or substituted cyclopentadienyl group (chemical formula 7), an unsubstituted or substituted indenyl group (chemical formula 8), or an unsubstituted or substituted fluorenyl group (chemical formula 9), provided that at least one of A and B is a group selected from an unsubstituted or substituted cyclopentaphenanthryl group, an unsubstituted or substituted benzindenyl group, or an unsubstituted or substituted indenyl group. Preferably, at least one of A and B is a group selected from an unsubstituted or substituted cyclopentaphenanthryl group or an unsubstituted or substituted benzindenyl group.

(Chemical Formula 2)

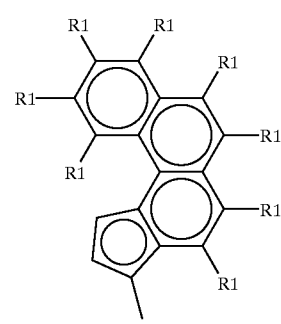

(Chemical Formula 3)

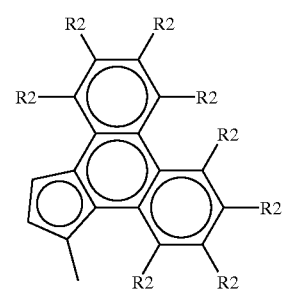

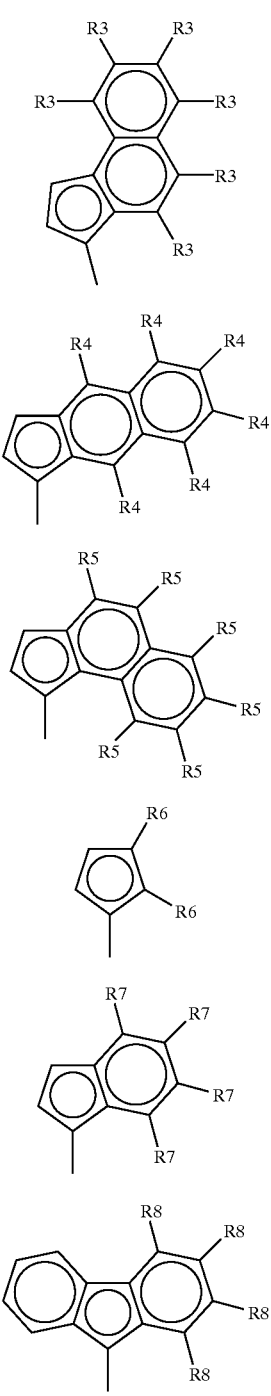

(Chemical Formula 4)

(Chemical Formula 5)

(Chemical Formula 6)

(Chemical Formula 7)

(Chemical Formula 8)

(Chemical Formula 9)

(in the above chemical formulae 2 to 9, each of $R_1$ to $R_8$ is hydrogen, a $C_{1-20}$ alkyl group, a $C_{6-10}$ aryl group, a $C_{7-20}$ alkylaryl group, a halogen atom, an $OSiR_3$ group, a $SiR_3$ group or a $PR_2$ group (each R is a $C_{1-10}$ hydrocarbon group), a plurality of $R_i$ may be the same or different from one another.) When each of A and B is an unsubstituted or substituted cyclopentaphenanthryl group, an unsubstituted or substituted benzindenyl group or an unsubstituted or substituted indenyl group, the two may be the same or different.

In the above chemical formula 2, Y is a methylene group, a silylene group or an ethylene group, which has bonds to A and B and which has hydrogen or a $C_{1-15}$ hydrocarbon group. The hydrocarbon group may, for example, be an alkyl group, an aryl group, a cycloalkyl group or a cycloaryl group. The substituents may be the same or different from one another.

Particularly preferably, Y is, for example, —$CH_2$—, —$CMe_2$—, —$CEt_2$—, —$CPh_2$—, a cyclohexylidene or cyclopentylidene group. Here, Me represents a methyl group, Et an ethyl group, and Ph a phenyl group.

In the above chemical formula 2, X is hydrogen, halogen, a $C_{1-15}$ alkyl group, a $C_{6-10}$ aryl group, a $C_{8-12}$ alkylaryl group, a silyl group having a $C_{1-4}$ hydrocarbon substituent, a $C_{1-10}$ alkoxy group, or a dialkylamide group having a $C_{1-6}$ alkyl substituent. The halogen may, for example, be chlorine or bromine; the alkyl group may, for example, be a methyl or ethyl; the aryl group may, for example, be a phenyl group; the alkylaryl group may, for example, be a benzyl group; the silyl group may, for example, be a trimethylsilyl group; the alkoxy group may, for example, be a methoxy group, an ethyoxy group or an isopropoxy group; and the dialkylamide group may, for example, be a dimethylamide group.

M is zirconium, hafnium or titanium. Particularly preferred is zirconium.

The co-catalyst to be used in the present invention may be a co-catalyst which has heretofore been commonly used in combination with a transition metal compound. As such a co-catalyst, aluminoxane (or alumoxane) or a boron compound is suitably used.

Such a boron compound and the above organic aluminum compound may be used at the same time. Especially when a boron compound is used as a co-catalyst, it is effective to add an alkyl aluminum compound such as triisobutylaluminum in order to remove impurities which adversely affect polymerization, such as water contained in the polymerization system.

The aromatic vinyl compound constituting the aromatic vinyl compound/α-olefin random copolymer to be used in the present invention, may, for example, be styrene and various substituted styrenes, such as p-methylstyrene, m-methylstyrene, o-methylstyrene, o-t-butylstyrene, m-t-butylstyrene, p-t-butylstyrene and α-methylstyren. These compounds may be used in combination. Further, a compound having a plurality of vinyl groups in one molecule, such as divinylbenzene, may be mentioned.

Industrially preferred is styrene or p-methylstyrene, and particularly preferably, styrene is employed.

The α-olefin constituting the aromatic vinyl compound/α-olefin random copolymer to be used in the present invention may suitably be a $C_{2-20}$ α-olefin, such as ethylene, propylene, 1-butene, 1-hexene, 4-methyl-1-pentene, 1-octene, or a cyclic olefin such as norbornene or norbornadiene. Further, these olefins may be used in combination of two or more of them.

Industrially, ethylene or propylene is preferred, particularly preferably, ethylene is employed.

As a production method for the aromatic vinyl compound/α-olefin copolymer as described here, a known method may be employed wherein the above exemplified α-olefin, the aromatic vinyl compound and the catalyst are contacted at a certain predetermined temperature.

The polymerization method is not particularly limited, and it may, for example, be a method for bulk polymerization in a liquid monomer or a method for solution polymerization in a single or mixed solvent selected from a saturated aliphatic or aromatic hydrocarbon or a halogenated hydrocarbon, such as pentane, hexane, heptane, cyclohexane, benzene, toluene, xylene, chloro-substituted benzene, chloro-substituted toluene, methylene chloride or chloroform. Further, the polymerization type may suitably be selected from batch polymerization, continuous polymerization, batch type polymerization, preliminary polymerization or gas phase polymerization, or a combination thereof.

The polymerization temperature for the aromatic vinyl compound/α-olefin copolymer using a transition metal compound as a catalyst, is properly from −78° C. to 200° C., preferably from 0 ° C. to 160 ° C. The polymerization temperature lower than −78° C. is industrially disadvantageous, and if it exceeds 200° C., decomposition of the transition metal compound tends to take place, such being undesirable. Further, industrially particularly preferably, it is from 30° C. to 160° C.

The amount of the transition metal compound to be used, is preferably such that the molar ratio of double bonds of the total charged monomers to the transition metal atoms in the transition metal compound, i.e. the molar ratio of double bonds of the total charged monomers/transition metal atoms, is from 1 to $10^8$.

When methyl alumoxane is used as the co-catalyst, the molar ratio of aluminum atoms in the methyl alumoxane to the transition metal atoms in the transition metal compound i.e. the molar ratio of aluminum atoms/transition metal atoms is from 0.1 to 100,000, preferably from 10 to 10,000.

When a boron compound is used as the co-catalyst, it is employed in a molar ratio of boron atoms/transition metal atoms of from 0.01 to 100, preferably from 0.1 to 10. If the molar ratio is smaller than this range, the transition metal compound can not be effectively activated, and if it exceeds this range, such will be economically disadvantageous.

The transition metal compound and the co-catalyst may be mixed or formulated outside the polymerization tank or may be mixed in the tank at the time of polymerization.

As an example, the random copolymer produced by means of the transition metal compound as described above, has characteristics in its chain structure and stereo regularity, and the details are disclosed in EP-A-0872429A2 or JP-A-9-309925 by the present inventors. Also with respect to the transition metal compound catalyst and the co-catalyst to be employed for the production, details are disclosed in the same publications.

Further, for the aromatic vinyl compound/α-olefin random copolymer obtained by this method, the amount of the catalyst used in the polymerization is very small, and accordingly, the catalyst component remaining in the formed copolymer is also extremely little, and the residual impurities are accordingly little, and also from this aspect, it is preferred that in the medical use, a medical material and a medical device with a high level of safety can be provided.

Of the aromatic vinyl compound/α-olefin random copolymer to be used in the present invention, the constituting components are not necessarily limited only to the aromatic vinyl compound and the α-olefin, and other monomers may be copolymerized, within a range not to impair the performance. Other monomers to be copolymerized may, for example, be a $C_{3-20}$ α-olefin such as propylene other than those selected above, a $C_{5-20}$ cyclic olefin such as norbornene, or a diene compound such as butadiene, 1,4-hexadiene, 1,5-hexadiene, ethylidene norbornene or vinyl cyclohexene. Further, two or more types of the above mentioned aromatic vinyl compounds may be copolymerized.

Further, depending upon the polymerization conditions, etc., the aromatic vinyl compound may contain a small amount of an atactic homopolymer formed by thermal, radical or cationic polymerization. However, such an amount is not higher than 10 wt % of the whole, and such a homopolymer can be removed by solvent extraction. However, if there is no particular problem from the viewpoint of the physical properties, the material may be used as it contains such a homopolymer.

In the medical material and the medical device of the present invention, a plasticizer (B) is blended to the resin component (A) for the purpose of adjusting the flexibility, the temperature dependency of physical properties, etc. As such a plasticizer, a known-plasticizer may be employed. For example, it is possible to add at least one member selected from a phthalic acid ester, a pyromellitic acid ester, a trimellitic acid ester, a trimesinic acid ester, a benzoic acid ester, an adipic acid ester, an azelaic acid ester, a sebacic acid ester, a malic acid ester compound, an epoxy compound, a polyester compound and an aromatic or aliphatic hydrocarbon oil.

As a preferred plasticizer, a low molecular weight organic ester type compound and a hydrocarbon may be employed. Among them, particularly preferred are the following phthalic acid ester type plasticizers.

Taking into consideration the bleeding property, influences over the human bodies, etc. totally, specific examples of preferred plasticizers may be dimethyl phthalate, diethyl phthalate, dibutyl phthalate, di-n-octyl phthalate, di-n-decyl phthalate, di-n-lauryl phthalate, undecyl phthalate, tetra-n-octyl pyromellitate, tri-n-octyl pyromellitate, triisooctyl trimellitate, tri-2-ethylhexyl trimellitate, trimellisic acid tri (2,2-dimethylpentyl)ester, trimesic acid tri(2-ethylhexyl) ester, benzoic acid diester, di-2-ethylhexyl adipate, diisodecyl adipate, dicapryl adipate, di-2-ethylhexyl azelate, di-2-ethylhexyl sebacate, dibutyl sebacate, tricresyl phosphate, triphenyl phosphate, diphenylcresyl phosphate, tributyl phosphate, dioctyl epoxyhexahydrophthalate, epoxidized soybean oil, methyl epoxy stearate, adipic acid type polyester, and sebacic type polyester.

With respect to the molecular weight of the plasticizer (B), there is no particular limitation. However, with respect to a low molecular organic ester type compound, it is preferably from 250 to 800, more preferably from 300 to 600.

If the molecular weight is too low, there will be a problem of volatilization, and if the molecular weight is too high, the molecules tend to hardly move in the composition, and particularly in the application to a blood bag, it tends to hardly elute into an erythrocyte-containing liquid, and consequently, an action to protect erythrocytes (hemolysis inhibition action) tends to be small.

The amount of the plasticizer (B) to be blended is from 0.1 to 200 parts by weight, preferably from 0.5 to 100 parts by weight, more preferably from 1 to 50 parts by weight, per 100 parts by weight of the resin composition (A) containing the aromatic vinyl compound/α-olefin random copolymer.

Further, for a blood bag, addition of a plasticizer is preferred from the viewpoint of the hemolysis inhibition action.

In the medical material and the medical device of the present invention, other thermoplastic resins may be incorporated in the resin component (A) constituting them, within a range of at most 50 wt %, as the case requires.

The thermoplastic resins to be blended are not particularly limited, and a styrene type resin, an olefin type resin, a polyester such as polycarbonate, polyethylene phthalate or polybutylene phthalate, an aromatic resin such as polyphenylene ether (PPE) or polyphenylene sulfide (PPS), a polyamide such as 6,6-nylon or 6-nylon, a methacrylic resin, an acrylic resin, an ethylene/vinyl acetate copolymer, a polymer such as EVA, or an elastomer or rubber, may be blended.

The styrene type resin may specifically be, for example, polystyrene, rubber-reinforced polystyrene (high impact polystyrene), an acrylonitril/styrene copolymer (AS resin), a styrene/mathacrylate copolymer such as a styrene/methyl methacrylate copolymer (MS resin), an acrylonitrile/butadiene/styrene copolymer (ABS resin), a rubber-reinforced MS resin, a maleic anhydride/styrene copolymer, a maleic anhydride/acrylonitrile/styrene copolymer, an acrylonitrile/a-methyl styrene copolymer, a methacrylnitrile/styrene copolymer or a methyl methacrylate/acrylonitrile/styrene copolymer.

The olefin type resin may specifically be, for example, a homopolymer such as polyethylene (PE) or polypropylene (PP), a block or random copolymer with butene, hexene, octene or the like, polymethylpentene, polybutene-1, a propylene/butene-1 copolymer, an ethylene/methacrylic acid or its ester copolymer, an ethylene/acrylic acid or its ester copolymer, or an ethylene/propylene copolymer (EPR).

The methacrylic resin may specifically be, for example, polymethacrylate (PMMA) or a methyl methacrylate/methacrylic acid copolymer.

Among the above, a styrene type resin or an olefin type resin is particularly preferred.

In the present invention, the elastomer or rubber to be blended, is not particularly limited. A styrene type or olefin type thermoplastic elastomer, and a thermoplastic elastomer or rubber, such as rubber, natural rubber, isoprene rubber, polyisobutyrene, EPR, acrylic rubber, neoprene rubber, polyester type elastomer or polyamide type elastomer, may, for example, be mentioned. These materials may be used alone or in combination of a plurality of them.

Examples of the styrene type elastomer or rubber include a styrene/butadiene block copolymer (SBS), a styrene/isoprene block copolymer (SIS) and hydrogenation products thereof, such as styrene/ethylene/butylene block copolymer (SEBS), a styrene/ethylene/propylene block polymer (SEPS), a styrene/butadiene rubber (SBR) and a styrene/butadiene/methyl methacrylate copolymer (MBS).

Among them, particularly preferred is a styrene type or olefin type elastomer or rubber. Further, the medical material or a medical device of the present invention may be used as closslinked by a conventional closslinking method by means of e.g. a peroxide or electron beam, as the case requires.

Further, a modification such as grafting, hydrogenation or addition of a functional group may be made to the aromatic vinyl compound/α-olefin random copolymer to be used for the medical material or the medical device of the present invention, by a conventional technique in this field. With respect to the medical material or the medical device of the present invention, such as a tube, a catheter, a bag or a container, an anti-fogging agent may be incorporated to the resin composition (C) prior to molding, which comprises the resin component (A) and the plasticizer (B), as the case requires, for the purpose of preventing fogging of the medical device by condensation of moisture in air on its surface to make it difficult to see the content. Otherwise, a method of coating such an anti-fogging agent on the surface of the medical device may also be effective.

As the anti-fogging agent, one commonly employed may be used as it is. For example, a sorbitan fatty acid ester, a glycerol fatty acid ester, a polyglycerol fatty acid ester, a fatty acid amine or a fatty acid amide may be mentioned.

Among them, a glycerol fatty acid ester, a polyglycerol fatty acid ester, a polyoxyalkylene ether or a fatty acid amine is particularly preferred.

The amount of the anti-fogging agent is at most 10 parts by weight, preferably from 0.5 to 8 parts by weight, more preferably from 1 to 5 parts by weight, par 100 parts by weight of the resin composition (C).

With respect to the medical material or the medical device of the present invention, various additives such as an antioxidant, an ultra violet absorber, a light stabilizer and a colorant, may be added to the resin composition (C), as the case requires. The amount of such additives is usually within a range of at most 5 parts by weight per 100 parts by weight of the resin composition (C).

In its application, the medical material or the medical device is used in various forms such as a film, a sheet, a catheter, a tube, a container, etc. The required mechanical strength varies depending upon the respective applications.

For the medical material or the medical device comprising the aromatic vinyl compound/α-olefin random copolymer of the present invention, it is possible to provide a medical material or the medical device having a wide range of physical properties by changing the content of the aromatic vinyl compound in the copolymer and the amount of the plasticizer incorporated.

For example, a nutrition catheter is required to have flexibility and low hardness to facilitate its insertion into the body. Further, the tube will be pulled repeated by the peristaltic motion, and accordingly, if the permanent elongation of the material is large, the surface tends to loosen to cause slackening of blood flow, which is likely to cause a blood clot. Therefore, the copolymer is desired to be one having a breaking elongation of at least 200% and a permanent elongation of at most 60%. For example, copolymers P-1 to P-3, which will be described hereinafter, may be mentioned. In a case where it is required to see the content, transparency will be required, and copolymers P-6 to P-8 may, for example, be mentioned.

When the above mentioned aromatic vinyl/α-olefin random copolymer obtainable by means of a transition metal compound of the chemical formula 1 as described above, is employed, the medical material or the medical device of the present invention is excellent in flexibility and particularly excellent in transparency and thus shows a haze value of at most 20% when made into a sheet having a thickness of e.g. 1 mm.

Heretofore, a medical device made of soft vinyl chloride has been sterilized usually by means of ethylene oxide gas (EOG). However, an adverse effect to the patient due to the remaining EOG is worried, and it is desired to eliminate the influence of the remaining EOG, and switching to other sterilization methods is conceivable. To the medical material or the medical device of the present invention, a gamma ray sterilization method can be applied, which is preferred in that no residue will remain by this method. The gamma ray sterilization method is convenient in that a closslinking reaction can be carried out at the same time as sterilization. Further, the medical material or the medical device of the present invention provides good biocompatibility. It is particularly excellent in blood compatibility. Especially in an application for insertion into a blood vessel, the medical device of the present invention is capable of imparting an antithrombotic property to its wetted surface. As a method of imparting the antithrombotic property, a known method may be employed. For example, e.g. heparine or urokinase may be fixed to the reactive functional groups of the catheter base material by covalent bonds, ionic bonds or adsorption.

With respect to the medical material or the medical device of the present invention, a method to obtain the resin composition (C) prior to molding, i.e. a method to obtain a resin composition (C) by mixing the resin component (A) and the plasticizer (B), and if necessary, other additives, is not particularly limited, and a conventional technique may be employed. For example, dry blending can be carried out by means of e.g. a Henschel mixer, a ribbon blender, a super mixer or a tumbler, or melt mixing may be carried out by means of a single screw or twin screw extruder, a Banbury mixer, a plastmill, a co-kneader or a roll mill. If necessary, such a method can be carried out in an inert gas atmosphere such as nitrogen. The form may be selected from e.g. a powder form, a pellet form, a strand form or a chip form.

In the present invention, a method for producing a medical device from the resin composition (C) may suitably be selected depending upon the shape of the medical device. For example, a known forming method such as extrusion molding, injection molding, compression molding, blow molding, rotational molding, calender forming, thermoforming or cast molding may be mentioned. A plurality of forming methods may be used in combination.

For the production of a multilayer sheet, a lamination method may also be employed. Further, in order to prevent blocking between sheets, the inner surface or the outer surface of a container may be roughened i.e. embossed, or an anti-blocking agent or a slipping agent may, for example, be added.

In either forming method, the principle of the method is such that the material is heated, melted or softened, whereupon it is deformed by an external force to a desired shape, and the fluidity of the material and the behavior in the molding process by the external force will influence over the physical properties of the formed product. Incorporation of a plasticizer serves effectively to improve such forming properties.

When the medical device of the present invention is, for example, a blood bag, an infusion solution bag or a dialysis bag, the sheet material for such a bag may be a single layer or a laminate containing the resin composition comprising the resin component (A) and the plasticizer (B), as a formed layer. This means that the sheet material may be composed solely of the resin composition (C) in the present invention or may be a laminate comprising at least one layer made of the resin composition (C) and at least one layer made of other resin component.

In the case of a laminate, layers made of other resin components are used for the purpose of the adjusting or improving e.g. the mechanical properties, forming properties, heat sealing properties, blocking resistance and heat resistance of the bag.

The resin components for forming the layers of other resin components, as the resin components for forming layers of a laminate, may, for example, be polyethylene, an ethylene/vinyl acetate copolymer, an ethylene/acrylate copolymer, polypropylene, poly-4-methylpentene-1, polyamide, polyether amide (a block copolymer of polyether and polyamide), polyurethane and a thermoplastic polyester.

In the laminate, the thicknesses of the polymer layers as formed layers, are important. Especially, in the case of a blood bag, leaching out of the plasticizer component (B) is important when other resin component is used as a formed layer for the inner layer which is in contact with the blood, and the layer should better be as thin as possible within an allowable range, preferably at most 0.08 mm, more preferably at most 0.05 mm.

When used for a laminate, the amount of the plasticizer (B) is selected particularly within a range of from 5 to 50 parts by weight in the range as described above, although it varies depending upon the types of the resin component (A) and the plasticizer component (B), or upon a single layer or laminate. Further, in the case of a laminate, the plasticizer component (B) should preferably be relatively large in amount. Further, the thickness of the entire sheet constituting the bag is preferably from 0.08 to 0.6 mm, more preferably from 0.1 to 0.5 mm, from the viewpoint of the strength, processability and operation efficiency.

Now, medical devices according to the present invention will be described.

Medical devices such as catheters to be inserted into a respiratory tract, a trachea, a digestive tract, a urethra, a blood vessel or other body cavities or systems, are required to have smoothness so that they can be certainly inserted to the desired sites without damaging the systems. Further, coating of a lubricative resin may be formed on the entire surface of the base material when an excellent lubricity is required on the surface in order to avoid damages to a mucous membrane or inflammation due to friction during the retention in the system. For example, such coating may be formed by covalent bonding of a water soluble polymer such as a maleic anhydride type polymer.

Utilizing the above described characteristics, the medical devices of the present are used, for example, as medical devices such as catheters e.g. indwelling catheters or balloon catheters, artificial blood vessels, circuits, syringes, artificial dialysers, blood component separators, artificial lungs or wound dressings, or as medical products such as sanitary goods e.g. menstrual sanitary products or paper diapers, surgical clothings or disposable sheets for hospital use. Among them, they are preferably used as medical devices to be used in contact with a body fluid, especially blood, such as medical tubes, catheters, artificial blood vessels, circuits, syringes, blood dialysers, blood component separators or artificial lungs, utilizing their excellent biocompatibility. With these medical devices, it is not necessary that the entire portion is formed of the medical material of the present invention, and it is sufficient that at least the portion which is in contact with the body fluid is formed of the medical material of the present invention. For example, with the above mentioned tubes, catheters or blood bags, the portion which is in contact with the body fluid is formed by the medical material of the present invention, and a portion which is not in contact with the body fluid may be formed of another resin to be used for medical use, such as polyurethane. Further, a medical container may be mentioned as one of the medical devices of the present invention, and it is preferably employed in an application where excellent flexibility and transparency are required.

The medical devices will be exemplified more specifically.

A. Intravascular insertion or indwelling catheters such as angiography catheters, cerebrovascular treating catheters, thermodilution catheters, IVH catheters or indwelling needles, or directers, stylettes, introducers or guide wires for these catheters.

B. Various balloons or balloon catheters.

C. Catheters to be orally or nasally inserted or retained in digestive organs, such as gastric tube catheters, nutrition catheters or tubes for supplying nutrition.

D. Oxygen catheter, oxygen cannula, tubes or cuffs for endotracheal tubes, tubes or cuffs for tracheotomy tubes, or catheters to be orally or nasally inserted or retained, such as endotracheal suction catheters.

E. Catheters to be inserted or retained in various body cavities or systems, such as suction catheters, waste liquid catheters, abdominal catheters, rectum catheters, urethral catheters or trocar tubes.

F. Endoscopic tubes to be inserted in various body cavities.
G. Stents, or artificial blood vessels, artificial tracheae, artificial bronchial tubes or artificial anus.
H. Various medical appliances such as artificial lungs, artificial hearts, artificial kidneys, reservoirs, bubble traps or drip chambers, or hearts to constitute extracorporeal circulation circuits such as circuit tubes forming blood flow paths.
I. Bags such as blood bags, infusion solution bags, injection liquid bags or waste liquid bags, or parts such as tubes or connectors to be connected to such bags.
J. Inspection instruments or treatment instruments which are required to have low friction resistance (lubricity) during retention in the bodies or during sliding, or inspection instruments or treatment instruments which are required to have antithrombotic properties.
K. Various gas supply tubes, or liquid supply tubes.
L. Contact lenses.

BEST MODE FOR CARRYING OUT THE INVENTION

Now, the present invention will be described in further detail with reference to Examples. However, these Examples by no means restrict the present invention.

In the following description, Ind represents a 1-indenyl group, BInd a 4,5-benz-1-indenyl group, CpPhen a 3-cyclopenta[c] phenanthrene group, Flu a 9-fluorenyl group, Me a methyl group, Et an ethyl group, tBu a tertiary butyl group, and Ph a phenyl group.

The analyses of copolymers obtained in various Examples and Comparative Examples were carried out by the following methods, and $^{13}C$-NMR spectra were measured by means of α-500 or JNMGX-270, manufactured by Nippon Denshi KK using a deuterated chloroform solvent or a deuterated 1,1,2,2-tetrachloroethane solvent and using TMS as standard.

Here, the measurement using TMS as standard is the following measurement. Firstly, using TMS as standard, a shift value of the center peak of the triplet $^{13}C$-NMR peak of deuterated 1,1,2,2-tetrachloroethane was determined. Then, the copolymer was dissolved in deuterated 1,1,2,2-tetrachloroethane, and $^{13}C$-NMR was measured, and various peak shift values were calculated using the triplet center peak of deuterated 1,1,2,2-tetrachloroethane as standard. The shift value of the triplet center peak of deuterated 1,1,2,2-tetrachloroethane was 73.89 ppm.

The $^{13}C$-NMR spectrum measurement for determination of a peak area was carried out by a NOE eliminated proton gate decoupling method using a pulse with a pulse width of 45° and a repetition time of 5 seconds as standard.

Whereas, the measurement was tried under the same conditions by changing the repetition time to 1.5 seconds, whereby the obtained value of the peak area of the copolymer agreed to the case where the repetition time was 5 seconds, at an error tolerance level.

Determination of the styrene content in the copolymer was carried out by $^{1}H$-NMR, and as the instrument, a-500 manufactured by Nippon Denshi KK and AC-250 manufactured by BRUCKER CO. using a deuterated chloroform solvent or a deuterated 1,1,2,2-tetrachloroethane solvent and TMS as standard, the comparison of intensities of the peak (6.5–7.5 ppm) attributable to a phenyl group proton and the proton peak (0.8–3 ppm) attributable to an alkyl group, was carried out.

With respect to the molecular weights in Examples, weight average molecular weights as calculated as standard polystyrene were obtained by means of GPC (gel permeation chromatography).

A copolymer soluble in THF at room temperature, was measured by HLC-8020, manufactured by TOSOH CORPORATION employing THF as the solvent.

A copolymer insoluble in THF at room temperature, was measured by 150CV apparatus manufactured by Waters Co. at 135° C using 1,2,4-trichlorobenzene as a solvent.

The DSC measurement was carried out by means of DSC200 manufactured by Seiko Denshi KK in a $N_2$ stream at a temperature raising rate of 10° C./min.

The mechanical strength, flexibility, transparency and biocompatibility of the copolymers and the resin compositions obtained in Examples were carried out by the following methods, respectively.

Mechanical Strength of a Formed Product

A sheet having a thickness of 1 mm was prepared, and from this sheet, a JIS No.2 test piece was punched out. Using this test piece, the tensile modulus, the breaking elongation, the yield point strength, the breaking strength, the 100% modulus and the 300% modulus were obtained at a tensile speed of 100 mm/min and used as indices for the mechanical strength.

Permanent Elongation

A sample pressed to a thickness of 1 mm as mentioned above, was punched out into a No.2 dumbbell, which was stretched 100% (2 cm) between the marked lines of 1 cm and maintained as stretched for 10 minutes, whereupon it was released and left to stand for 10 minutes, and the length between the reference lines was measured to determine the residual permanent strain. The permanent elongation was represented by the ratio (%) of the elongation to the initial length.

Flexibility

A sheet having a thickness of 2 mm was prepared, and in accordance with a dulometer hardness testing method of JIS K-7215, dulometer hardness of types D and A was obtained and used as an index for flexibility.

Transparency of a Formed Product

A sheet having a thickness of 1 mm was prepared, and the haze was obtained by means of a turbidity meter NDH-2000, manufactured by Nippon Denshoku KK by a method prescribed in JIS K-7361-1.

MFR

Was measured in accordance with a thermoplastic flow test method of JIS K-7210. The measurement was carried out at a measuring temperature of 200° C. under a test load of 5 kgf.

Blood Compatibility

A sheet having a thickness of 1 mm was prepared, and the obtained sheet was cut into a size of 1 cm×1 cm to obtain a test piece. This test piece was immersed at 37° C. for 30 minutes in a heparin-added whole blood prepared by adding heparin sodium salt to human blood after blood sampling, to bring the concentration to 5 IU/ml. This test piece was taken out from the heparin-added whole blood and washed with a physiological sodium chloride aqueous solution. Then, the surface was treated by means of glutaraldehyde and osmium oxide for fixing, and the obtained sample was inspected by means of an electron microscope, whereby the number of blood platelets deposited on the surface of the test piece was counted and used as an index for blood compatibility. The smaller the number of blood platelets deposited on the surface of the test specimen, the better the blood compatibility.

PREPARATION EXAMPLES

Preparation of Transition Metal Catalyst Components A and B

Transition metal catalyst components A [rac dimethylmethylenebis(4,5-benz-1-indenyl)zirconium dichloride] and B [rac dimethylmethylene(4,5-benz-1-indenyl) (1-indenyl)zirconium dichloride] were prepared by the method disclosed in EP-A-0872492A2.

Preparation of Transition Metal Catalyst Component C

The rac-dimethylmethylenebis(3-cyclopenta[c] phenanthryl)zirconium dichloride of the following formula (another name: rac{CpPhen-CMe$_2$-CpPhen}ZrCl$_2$) was prepared as follows. Here, CpPhen represents 3-cyclopenta[c] phenanthryl).

(Chemical Formula 10)

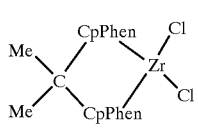

1H or 3H-cyclopenta[c]phenanthrene was prepared in accordance with the method disclosed in a literature Organometallics, 16, 3413 (1997). C-1 isopropylidenebis (cyclopenta[c]phenanthrene)

In an Ar atmosphere, 32 mmol 1H or 3H-cyclopenta[c] phenanthrene was added to 40 ml of dimethoxyethane having 3.0 g of potassium hydroxide suspended therein, followed by stirring at room temperature for 30 minutes. Then, 15 mmol of acetone was added, followed by stirring at 60° C. for two hours.

After neutralization by an addition of a 10% phosphoric acid aqueous solution, the mixture was extracted with methylene chloride, and the organic layer was washed with water and dried, and methylene chloride was distilled. By recrystallization from a methylene chloride/diethylether solution, 1.5 g of white crystal isopropylidenebis(cyclopenta[c] phenanthrene) was obtained.

From the $^1$H-NMR spectrum measurement, it has peaks at positions of 1.98 ppm (6H,s), 4.20 ppm (4H,t), 6.89 ppm (2H,t), 7.5–7.9 ppm (14H,m), 8.91 ppm (2H,d).

The measurement was carried out using TMS as standard and CDCl$_3$ as a solvent.

C-2 preparation of rac-dimethylmethylenebis(3-cyclopenta [c]phenanthryl)zirconium dichloride In an Ar stream, 2.0 mmol of isopropylidenebis cyclopenta[c]phenanthrene) and 2.0 mmol of zirconium tetrakisdimethylamide{Zr(NMe2)4} were charged together with 20 ml of toluene and stirred for 7 hours under reflux. Under reduced pressure, toluene was distilled off, and 50 ml of methylene chloride was added, followed by cooling to −50° C. 4.0 mmol of dimethylamine hydrochloride was slowly added, and the mixture was slowly heated to room temperature and further stirred for two hours. The solvent was distilled off, and then the obtained solid was washed with pentane and then with a small amount of methylene chloride to remove the meso form and the ligand to obtain 0.36 g of yellowish orange crystals of rac-dimethylmethylenebis(3-cyclopenta[c] phenanthryl) zirconium dichloride. From the $^1$H-NMR spectrum measurement, it has peaks at positions of 2.55 ppm (6H,s), 6.49 ppm (2H,d), 7.55–8.02 ppm (16H,m), 8.82 ppm (2H,d).

The measurement was carried out using TMS as standard and CDCl$_3$ as a solvent.

Preparation of Transition Metal Compound D

With reference to JP-A-7-053168, CGCT (constrained geometrical structure) type Ti complex (tertiary butylamido) dimethyl(tetramethyl-72 5-cyclopentadienyl)silane titanium dichloride, another name {CpMe$_4$-SiMe$_2$-NtBu}TiCl$_2$ was prepared.

Preparation of Styrene/Ethylene Random Copolymer

Test Example 1

Preparation of Copolymer P-1

Polymerization was carried out by means of a polymerizer having a capacity of 150 l and equipped with a stirrer and a jacket for cooling and heating. 80 l of dehydrated cyclohexane and 5 l of dehydrated styrene were charged, followed by heating and stirring at an internal temperature of 40° C. 48 mmol of triisobutylaluminum and 840 mmol, based on Al, of methylalumoxane (MMAO-3A, manufactured by Tosoh-Akzo KK) were added. Immediately, ethylene was introduced, and after the system was stabilized under a pressure of 1 MPa, about 100 ml of a toluene solution having 79 umol of the catalyst rac-dimethylmethylenebis (4,5-benz-1-indenyl)zirconium dichloride obtained in the above Preparation Example, dissolved, was added to the polymerizer from a catalyst tank installed above the polymerization vessel. Immediately, heat generation started, and cooling water was introduced into the jacket. The internal temperature rose to the maximum of 71° C. and then gradually decreased and finally became 70° C. While maintaining the ethylene pressure at 1 MPa, polymerization was carried out for 3 hours.

The polymerization solution was fed over a period of one hour into 150 l of heated water which was heated to 85° C. and vigorously stirred and which contained a dispersant. Then, stirring was continued at 97° C. for one hour. Then, the hot water containing crumbs was fed into cool water, and the crumbs were recovered. The obtained crumbs were dried at 50° C. by blowing air. The results of the polymerization are shown in Table 2. The dried crumbs were formed into pellets by a Tandem extruding machine equipped with a hot cut pelletizer (Co-Kneader PLK-46, manufactured by Btiss CO.). The operation was carried out under the following conditions.

First extruder: cylinder temperature of 80° C., screw rotational speed of 120 rpm.

Second extruder: cylinder temperature of 120° C., die of 135° C., screw rotational speed of 22 rpm.

Test Examples 2 to 4

Preparation of Copolymers P-2 to P-4

Polymerization and post treatment were carried out in the same manner as in Test Example 1 under the conditions shown in Table 1.

Table 2 shows the styrene contents determined by the $^1$H-NMR measurements, the molecular weights obtained from the GPC measurements, the tacticities of the styrene-ethylene alternate structures obtained from the $^{13}$C-NMR measurements, the λ-values and the melting points obtained by the DSC measurements, of the copolymers obtained in the respective Test Examples and Comparative Test Examples.

Test Example 5

Preparation of Copolymer P-5

Polymerization was carried out by means of a autoclave having a capacity of 10 l and equipped with a stirrer and a jacket for cooling and heating.

2400 ml of dehydrated toluene and 2400 ml of dehydrated styrene were charged, followed by heating and stirring at an internal temperature of 50° C. About 100 l of nitrogen was bubbled to purge the interior of the system, and 8.4 mmol of triisobutylaluminum(TIBA) and 84 mmol, based on Al, of methylalumoxane (MMAO-3A, manufactured by Tosoh-Akzo KK) were added. Immediately, ethylene was introduced, and after the system was stabilized under a pressure of 10 kg/cm$^2$G, about 50 ml of a toluene solution having 8.4 mmol of a catalyst rac{CpPhen-C(Me)2-CpPhen}ZrCl$_2$ and 0.84 mmol of triisobutylaluminum dissolved, was added to the autoclave from a catalyst tank installed above the autoclave. The polymerization was carried out for one hour while maintaining the internal temperature at 50° C. and the ethylene pressure at 10 kg/cm$^2$G (1.1 MPa). During the polymerization, the reaction solution temperature and the consumption rate of ethylene were monitored by an integrating flow meter, and the polymerization was carried out until the polymerization reaction substantially terminated.

After completion of the polymerization, the obtained polymerization solution was gradually put into excess methanol which was vigorously stirred, to precipitate the formed polymer. The polymer was dried under reduced pressure at 60° C. until no more weight change was observed to obtain 409 g of a copolymer having a styrene content of 19 mol %.

The results are shown in Table 2.

Test Example 6
Preparation of Copolymer CP-1

Using a CGCT (constrained geometrical structure) type Ti complex (tertiary butylamido)dimethyl(tetramethyl-η5-cyclopentadienyl) silane titanium dichloride (Me4Cp-SiMe2-NtBuTiCl2: CGCT type catalyst) as the complex, polymerization was carried out under the conditions shown in Table 1.

Example 1 to 6

The copolymers obtained in Test Examples 1 to 6 were press-molded into a thickness of from 1 to 3 mm at 210° C., and the breaking strength, the permanent elongation, the flexibility and the transparency were evaluated. The results are shown in Table 3.

Example 7 and 8

Copolymers P-2 and P-4 obtained in Test Examples 2 and 4 were kneaded with di-n-decyl phthalate (DnDP) as a plasticizer in a weight ratio of 80:20 in a temperature range of from 160 to 170° C. by means of a twin screw melt kneading extruder within a temperature range of from 160 to 170° C., and extruded to obtain a strand, which was cooled with ice, cut and dried to obtain a pellet-form polymer composition. The obtained resin composition was evaluated in the same manner as described above.

The results are shown in Table 3.

Test Example 7 to 9
Preparation of Copolymers P-6 to P-8

Under the conditions shown in Table 4, polymerization and post treatment were carried out in the same manner as in Test Example 1.

Table 5 shows the styrene contents obtained from the $^1$H-NMR measurements, the molecular weights obtained from the GPC measurements, the molecular weight distributions, the tacticities of the styrene-ethylene alternative structures obtained from the $^{13}$C-NMR measurements, the λ-values, and the melting points obtained by the DSC measurements, of the copolymers obtained in the respective Test Examples. The results are shown in Table 5.

Test Example 10 to 12
Preparation of Copolymers CP-2 to CP-4

As a catalyst, transition metal compound D, CGCT (constrained geometrical structure) type Ti complex (tertiary butylamido)dimethyl(tetramethyl-72 5-cyclopentadienyl) silane titanium dichloride (Me4Cp-SiMe2-NtBuTiCl2:CGCT type catalyst) was used.

For the preparation of CP-2, polymerization and post treatment were carried out in the same manner as in Test Example 1 under the conditions shown in Table 4 by using a polymerizer having a capacity of 150 l and equipped with a stirrer and a jacket for cooling and heating.

For the preparation of CP-3 and CP-4, polymerization and post treatment were carried out in the same manner as in Test Example 5 under the conditions shown in Table 4 by using an autoclave having a capacity of 10 l and equipped with a stirrer and a jacket for cooling and heating.

The results are shown in Table 5.

Examples 9 to 14

The resin compositions obtained in Test Examples 7 to 12 were press-molded at 210° C. into a thickness of from 1 to 3 mm, whereupon the mechanical strength, the flexibility, the transparency and the permanent elongation were evaluated.

The results are shown in Table 6.

Comparative Examples 1 and 2

Using an ethylene/octene copolymer, EG8180 (manufactured by DuPont Dow Elastomer Co.) or LLDPE (Ultzex 1520L, manufactured by Mitsui Chemicals, Inc.), press molding was carried out in the same manner as in Examples 1 to 9, followed by evaluation. The results are shown in Table 6.

Examples 15 to 41

Copolymers P-6 to P-8 and CP-2 to CP-4, obtained by the above Test Examples were kneaded, respectively, with naphthene type oil NM280 (manufactured by Idemitsu Kousan KK), paraffin type oil PW-90 (manufactured by Idemitsu Kousan KK), ester type PL-100 and DOP (each manufactured by Mitsubishi Gas Chemical Co., Inc.), as plasticizers, in the proportions as shown in Tables 7 and 8, by means of a Brabender Plasti-Corder (manufactured by Brabender Co.) at 200° C. to obtain polymer compositions. The obtained resin compositions were evaluated in the same manner as described above. The results are shown in Tables 7 and 8.

Comparative Examples 3 to 6

EG8180 was kneaded with a plasticizer in the proportions as shown in Table 8 in the same manner as in Examples 15 to 41 to obtain pellet form polymer compositions. The obtained resin compositions were evaluated in the same manner as described above. The results are shown in Table 8.

Blood Compatibility

Examples 42 and 43

The copolymer resin compositions obtained in Test Examples 2 and 4 were extrusion-molded and heat-sealed to obtain bags of 15 cm×10 cm having a thickness of 0.5 mm. As a control, a test piece prepared by cutting a soft vinyl chloride sheet having a thickness of 1 mm into a size of 1 cm×1 cm, was used, and the blood compatibility was evaluated by the above described method. A concentrated blood platelet solution adjusted so that the concentration of blood platelets became 5 IU/ml, was put into the obtained bag, followed by shaking at 25° C. for 72 hours. The concentrated blood platelet solution was taken out from the bag, and the platelet aggregation was measured. In a case where shaking was carried out by using a bag produced by any one of the resin compositions, the platelet aggregation at the time of addition of collagen was 50%, and thus the platelet aggregation ability was maintained satisfactorily. From this, it is evident that the bags made of the resin compositions obtained in Test Examples 2 and 4 had good blood compatibility.

γ-Ray Sterilization Test

Examples 44 to 46 and Comparative Examples 7 and 8

Sheets having a thickness of 1 mm obtained by pressing in Examples 9 to 11, were put into polyethylene bags, which were respectively put into cardboard boxes. 25 kGray was irradiated, which was a usual sterilization condition for cardboard boxes. After the irradiation, the mechanical strength, the flexibility, Mw and MFR were measured. The results are shown in Table 9.

With copolymers, like PE, improvement in 100% modulus and 300% modulus and tendency for a decrease in elongation were observed after the irradiation, and it was considered that the crosslinking reaction took place.

Examples 47 to 51 and Comparative Example 9

(1) Preparation of Resin Compositions

Copolymers P-9 to P-11 shown in Table 10 and plasticizers PL-100, DnDP and BTHC, were kneaded in the proportions as shown in Table 10 by means of a twin screw melt kneading extruder within a temperature range of from 160 to 170° C and extruded to obtain resin compositions D-1 to D-5 of Table 11.

(2) Preparation of Sheets

Using P-9, P-10, P-11, D-1 to D-5 and soft vinyl chloride, each material was extruded at 170° C. from a die for single layer or multi layer, cooled by a casting roller maintained at 20° C. and then trimmed, and a sheet having a thickness of 0.28 mm and a width of 150 mm was wound up at a rate of 5 m/min.

(3) Preparation of Bags

Using this sheet, a rectangular test bag (capacity: 50 ml) having an effective surface area of about 80 cm² and an internal size of 50 mm×80 mm was prepared by a heat sealing method and subjected to ethylene oxide sterilization (65° C.×5 hours).

(4) Hemolysis Test 200 ml of human blood was sampled in a blood sampling bag containing an anticoagulant, and concentrated red cells (CRC) were formulated in accordance with a conventional method. 50 ml each of formulated CRC was aseptically put into a test bag by a clean work station and stored at 4° C. for three weeks, whereupon the amount of the plasma hemoglobin in each test bag was measured by a conventional method, and the hemolysis level was evaluated. The results are shown in Table 12.

It is evident that as compared with a control wherein a commonly employed soft vinyl chloride bag was used, Examples 47 to 51 wherein the resin compositions of the present invention were used, are comparable in their practical usefulness. It is evident that Comparative Example 9 constituted solely by a sheet containing no plasticizer, is inferior to Examples 47 to 51. Further, a soft vinyl chloride bag has a problem of an influence to the environment in its disposal treatment after use. Whereas, the blood bag of the present invention contains substantially no chlorine and thus is free from such a problem.

Biocompatibility Test

Examples 52 to 59

The styrene-ethylene random copolymers and resin compositions used in Examples 1 to 8 and a soft vinyl chloride as a control, were extrusion molded into tubes to obtain catheters having a length of 30 cm, an outer diameter of 2.6 mm and an inner diameter of 1.6 mm. Each of the obtained catheters was inserted into a rabbit jugular vein and retained for 7 days. At that time, the interior of the catheter was filled with a physiological sodium chloride aqueous solution, and the end which was exposed out of the body from the vein, was sealed. The catheter was taken out from the rabbit jugular vein and washed with a physiological sodium chloride aqueous solution, whereupon the surface was treated with glutaraldehyde and osmium oxide for fixing, and the outer surface of the catheter was inspected by naked eyes and by an electron microscope.

With a tube made of each of the styrene-ethylene random copolymers and resin compositions in Examples 1 to 8, fibrin and platelets of an equal or lower level as compared with the soft vinyl chloride as a contrast, were observed on the outer surface of the catheter.

TABLE 1

| | Copolymer | catalyst μmol | MAO mmol | TIBA mmol | St/CyH. l/l | Et pressure MPa | Polymerization temperature ° C. | Polymerization time hr |
|---|---|---|---|---|---|---|---|---|
| Test Example 1 | P-1 | B: 79 | 840 | 84 | 5/80 | 1.0 | 40–71 | 3 |
| Test Example 2 | P-2 | A: 91 | 252 | 84 | 5/80 | 1.0 | 40–57 | 3 |
| Test Example 3 | P-3 | A: 107 | 168 | 84 | 12/60 | 1.0 | 50–72 | 2.5 |
| Test Example 4 | P-4 | A: 83 | 840 | 84 | 18/54 | 1.0 | 40–51 | 1 |
| Test Example 5 | P-5 | C: 8.4 *1 | 84 | 8.4 | 2.4/2.4 toluene | 1.1 | 50–70 | 1 |

TABLE 1-continued

| | Copolymer | catalyst μmol | MAO mmol | TIBA mmol | St/CyH. l/l | Et pressure MPa | Polymerization temperature ° C. | Polymerization time hr |
|---|---|---|---|---|---|---|---|---|
| | | | | | | | Polymerization conditions | |
| Test Example 6 | CP-1 | D: 21 | 84 | 8.4 | 1.3/3.5 | 1.1 | 50 | 2.5 |

Catalyst:
B: rac dimethylmethylene(4,5-benz-1-indenyl)(1-indenyl)zirconium dichloride
A: rac dimethylmethylenebis(4,5-benz-1-indenyl)zirconium dichloride
C: rac dimethylmethylenebis(3-cyclopenta[c]phenanthryl)zirconium dichloride
D: (tert-butylamido)dimethyl(tetramethyl-η5-cyclopentadienyl)silane titanium dichloride
MAO: MMAO
CyH: Cyclohexane
*1: In Test Example 5 only, toluene was used as a solvent.

TABLE 2

| | Copolymer | St content Mol % | Mw × 10$^4$ | Mw/Mn mmol | Tacticity m-value *1 | λ-value | Melting point ° C. |
|---|---|---|---|---|---|---|---|
| Test Example 1 | P-1 | 10 | 13.0 | 2.3 | >0.95 | 6 | 79 |
| Test Example 2 | P-2 | 13 | 14.7 | 2.4 | >0.95 | 10 | 68 |
| Test Example 3 | P-3 | 25 | 21.8 | 2.2 | >0.95 | 15 | 51 |
| Test Example 4 | P-4 | 40 | 34.8 | 2.0 | >0.95 | 19 | Nil |
| Test Example 5 | P-5 | 19 | 9.2 | 1.9 | >0.95 | 6 | Nil |
| Test Example 6 | CP-1 | 13 | 18.7 | 1.5 | 0.5 | — | 63 |

— Not measured

TABLE 3

| | | Example 1 | Example 2 | Example 3 | Example 4 | Example 5 | Example 6 | Example 7 | Example 8 |
|---|---|---|---|---|---|---|---|---|---|
| P-1 | | 100 | | | | | | | |
| P-2 | | | 100 | | | | | 80 | |
| P-3 | | | | 100 | | | | | |
| P-4 | | | | | 100 | | | | 80 |
| P-5 | | | | | | 100 | | | |
| CP-1 | | | | | | | 100 | | |
| DnDP | | | | | | | | 20 | 20 |
| Breaking strength | (MPa) | 40.1 | 43.4 | 3.9 | 18.1 | 13.4 | 29.0 | 39.1 | 16.3 |
| Permanent elongation | (%) | 60 | 20 | 20 | 30 | 25 | 25 | 40 | 55 |
| Haze | (%) | 22.4 | 26.5 | 36.7 | 35.4 | 39.8 | 58.2 | 25.6 | 34.5 |
| Shore hardness D | (%) | 31 | 28 | 13 | 25 | 14 | 30 | 14 | 18 |

TABLE 4

| | Copolymer | catalyst μmol | MAO mmol | TIBA mmol | St/CyH. l/l | Et pressure MPa | Polymerization temperature ° C. | Polymerization time hr |
|---|---|---|---|---|---|---|---|---|
| Test Example 7 | P-6 | A: 84 | P: 17 | 84 | 4/68 | 0.9 | 50–81 | 2.5 |
| Test Example 8 | P-7 | A: 83 | P: 25 | 84 | 12/60 | 0.9 | 40–68 | 3 |
| Test Example 9 | P-8 | A: 98 | M: 840 | 84 | 18/54 | 0.9 | 40–44 | 3 |
| Test Example 10 | CP-2 | D: 329 | M: 440 | 86 | 18/54 | 0.9 | 53–63 | 3 |
| Test Example 11 | CP-3 | D: 21 | M: 84 | 8.4 | 4/0.8 | 1.0 | 70–73 | 2 |
| Test Example 12 | CP-4 | D: 42 | M: 42 | 8.4 | 4/0.8 | 0.3 | 60–61 | 2.5 |

Catalyst:
A: rac dimethylmethylenebis(4,5-benz-1-indenyl)zirconium dichloride
D: (tert-butylamido)dimethyl(tetramethyl-η5-cyclopentadienyl)silane titanium dichloride
MAO: methylalumoxane
P: PMAO (methylalumoxane, manufactured by Tosoh-Akzo, tradename: MMAO)
M: MMAO (methylalumoxane, manufactured by Tosoh-Akzo, tradename: PMAO)
CyH: Cyclohexane

TABLE 5

Polymerization results

|  | Copolymer | St content Mol % | Mw × 10⁴ | Mw/Mn mmol | Tacticity m-value *1 | λ-value | Melting point ° C. |
|---|---|---|---|---|---|---|---|
| Test Example 7 | P-6 | 16 | 19.4 | 2.3 | >0.95 | 11 | 62 |
| Test Example 8 | P-7 | 26 | 24.9 | 2.2 | >0.95 | 16 | 42 |
| Test Example 9 | P-8 | 43 | 40.5 | 1.9 | >0.95 | 56 | 85 |
| Test Example 10 | CP-2 | 17 | 24.6 | 2.2 | 0.5 | 7 | 57 |
| Test Example 11 | CP-3 | 24 | 24.6 | 2.5 | 0.5 | 7 | 42 |
| Test Example 12 | CP-4 | 45 | 26.5 | 2.0 | 0.5 | 25 | Nil |

*1 Isotactic diad fraction

TABLE 6

|  |  | Example 9 | Example 10 | Example 11 | Example 12 | Example 13 | Example 14 | Comp. Ex. 1 | Comp. Ex. 2 |
|---|---|---|---|---|---|---|---|---|---|
| P-6 |  | 100 |  |  |  |  |  |  |  |
| P-7 |  |  | 100 |  |  |  |  |  |  |
| P-8 |  |  |  | 100 |  |  |  |  |  |
| CP-2 |  |  |  |  | 100 |  |  |  |  |
| CP-3 |  |  |  |  |  | 100 |  |  |  |
| CP-4 |  |  |  |  |  |  | 100 |  |  |
| EG8180 |  |  |  |  |  |  |  | 100 |  |
| LLDPE |  |  |  |  |  |  |  |  | 100 |
| Breaking elongation | (%) | 723 | 763 | 447 | 493 | 453 | 320 | 737 | 750 |
| Yield point | (MPa) | — | — | — | — | — | 14.8 | — | 9.0 |
| Breaking strength | (MPa) | 33.3 | 6.8 | 16.0 | 40.4 | 17.0 | 25.0 | 19.5 | 41.2 |
| Tensile modulus | (MPa) | 7.1 | 3.0 | 8.9 | 12.3 | 4.7 | 348.7 | 5.6 | 85.9 |
| Permanent elongation | (%) | 15 | 20 | 15 | 10 | 10 | 65 | 30 | 100 |
| 100% modulus | (MPa) | 2.7 | 1.3 | 2.3 | 3.1 | 2.3 | 12.2 | 2.0 | 9.0 |
| 300% modulus | (MPa) | 4.5 | 1.7 | 4.6 | 6.0 | 5.6 | 23.2 | 2.7 | 9.4 |
| MFR | (200° C.) | 1.01 | 1.28 | 1.10 | 1.13 | 1.55 | 2.06 | 1.80 | 7.14 |
| Haze | (%) | 19.0 | 18.5 | 8.4 | 49.9 | 90.2 | 39.4 | 19.0 | — |
| Hardness | (Shore D) | 25 | 16 | 27 | 24 | 26 | 61 | 19 | 48 |
|  | (Shore A) | 78 | 60 | 77 | 74 | 70 | 98 | 71 | 97 |
| Tg | (° C.) | −28.2 | −38.6 | Nil | −17.4 | −14.3 | 22.1 | −59.7 |  |
| Tm | (° C.) | 62.4 | 42.0 | 74.9 | 85.1 | 42.0 | Nil | 48.4 |  |
| Vicat softening point | (° C.) | 59.4 | 44.8 | 54.2 | 58.1 | 48.1 | 53.6 | 51.0 |  |

(Ultozex 1520L, manufactured by Mitsui Chemical Co., Ltd.)

TABLE 7

|  |  | Example 15 | Example 16 | Example 17 | Example 18 | Example 19 | Example 20 | Example 21 |
|---|---|---|---|---|---|---|---|---|
| P-6 |  | 100 | 100 | 100 | 100 | 100 | 100 | 100 |
| P-7 |  |  |  |  |  |  |  |  |
| P-8 |  |  |  |  |  |  |  |  |
| CP-2 |  |  |  |  |  |  |  |  |
| CP-3 |  |  |  |  |  |  |  |  |
| CP-4 |  |  |  |  |  |  |  |  |
| EG8180 |  |  |  |  |  |  |  |  |
| NM-280 |  | 5 |  |  |  |  |  |  |
| PW-90 |  |  | 5 |  |  |  |  |  |
| PL-100 |  |  |  | 5 | 10 | 20 | 30 |  |
| DOP |  |  |  |  |  |  |  | 5 |
| Breaking elongation | (%) | 593 | 590 | 630 | 637 | 680 | 763 | 600 |
| Yield point | (MPa) | — | — | — | — | — | — | — |
| Breaking strength | (MPa) | 34.0 | 31.7 | 26.3 | 20.3 | 11.6 | 10.0 | 27.3 |
| Tensile modulus | (MPa) | 7.4 | 8.2 | 8.1 | 7.7 | 6.1 | 4.5 | 6.9 |
| Permanent elongation | (%) | 10 | 10 | 10 | 10 | 10 | 10 | 10 |

TABLE 7-continued

|  |  |  |  |  |  |  |  |  |
|---|---|---|---|---|---|---|---|---|
| 100% modulus | (MPa) | 2.9 | 2.7 | 2.7 | 2.6 | 2.2 | 1.7 | 2.7 |
| 300% modulus | (MPa) | 4.6 | 4.5 | 4.3 | 3.9 | 3.3 | 2.7 | 4.4 |
| MFR | (200° C.) | 1.70 | 2.70 | 2.73 | 4.42 | 13.10 | 27.17 | 3.52 |
| Haze | (%) | 14.4 | 18.0 | 16.1 | 20.6 | 25.4 | 35.4 | 15.7 |
| Hardness | (Shore D) | 26 | 23 | 20 | 21 | 17 | 14 | 24 |
|  | (Shore A) | 75 | 6 | 64 | 72 | 67 | 60 | 75 |
| Tg | (° C.) | −24.0 | −22.9 | −33.0 | −36.1 | −47.7 | −55.1 | −28.5 |
| Tm | (° C.) | 62.1 | 61.3 | 41.8 | 50.0 | 56.0 | 56.5 | 41.0 |
| Vicat softening point | (° C.) | 57.6 | 57.1 | 57.5 |  |  |  | 56.6 |

|  |  | Example 22 | Example 23 | Example 24 | Example 25 | Example 26 | Example 27 | Example 28 | Example 29 |
|---|---|---|---|---|---|---|---|---|---|
| P-6 |  |  |  |  |  |  |  |  |  |
| P-7 |  | 100 | 100 | 100 | 100 | 100 | 100 | 100 |  |
| P-8 |  |  |  |  |  |  |  |  | 100 |
| CP-2 |  |  |  |  |  |  |  |  |  |
| CP-3 |  |  |  |  |  |  |  |  |  |
| CP-4 |  |  |  |  |  |  |  |  |  |
| EG8180 |  |  |  |  |  |  |  |  |  |
| NM-280 |  | 5 |  |  |  |  |  |  | 5 |
| PW-90 |  |  | 5 |  |  |  |  |  |  |
| PL-100 |  |  |  | 5 | 10 | 20 | 30 |  |  |
| DOP |  |  |  |  |  |  |  | 5 |  |
| Breaking elongation | (%) | 537 | 547 | 570 | 600 | 660 | 697 | 570 | 397 |
| Yield point | (MPa) | — | — | — | — | — | — | — | 3.0 |
| Breaking strength | (MPa) | 7.9 | 7.5 | 5.5 | 6.4 | 10.9 | 11.6 | 6.7 | 27.9 |
| Tensile modulus | (MPa) | 3.2 | 3.0 | 2.9 | 3.2 | 3.8 | 3.4 | 2.6 | 41.8 |
| Permanent elongation | (%) | 10 | 10 | 10 | 15 | 10 | 5 | 10 | 5 |
| 100% modulus | (MPa) | 1.5 | 1.4 | 1.4 | 1.2 | 1.2 | 1.2 | 1.3 | 2.7 |
| 300% modulus | (MPa) | 2.1 | 1.9 | 1.7 | 1.6 | 1.7 | 1.8 | 1.7 | 5.0 |
| MFR | (200° C.) | 2.14 | 2.18 | 2.38 | 4.54 | 9.04 | 16.21 | 2.33 | 1.67 |
| Haze | (%) | 26.5 | 21.2 | 24.6 | 34.1 | 36.1 | 38.7 | 25.0 | 13.3 |
| Hardness | (Shore D) | 16 | 13 | 15 | 14 | 14 | 12 | 17 | 31 |
|  | (Shore A) | 59 | 55 | 56 | 58 | 59 | 55 | 58 | 80 |
| Tg | (° C.) | −8.9 | −20.7 | −21.3 | −25.4 | −33.6 | −41.4 | −21.0 | −25.5 |
| Tm | (° C.) | 4.0 | 41.8 | 41.8 | 32.7 | 14.1 | 25.0 | 39.4 | 22.2 |
| Vicat softening point | (° C.) | <40 | <40 | <40 |  |  |  | <40 | 47.7 |

TABLE 8

|  |  | Example 30 | Example 31 | Example 32 | Example 33 | Example 34 | Example 35 |
|---|---|---|---|---|---|---|---|
| P-6 |  |  |  |  |  |  |  |
| P-7 |  |  |  |  |  |  |  |
| P-8 |  | 100 | 100 | 100 | 100 | 100 | 100 |
| CP-2 |  |  |  |  |  |  |  |
| CP-3 |  |  |  |  |  |  |  |
| CP-4 |  |  |  |  |  |  |  |
| EG8180 |  |  |  |  |  |  |  |
| NM-280 |  |  |  |  |  |  |  |
| PW-90 |  | 5 |  |  |  |  |  |
| PL-100 |  |  | 5 | 10 | 20 | 30 |  |
| DOP |  |  |  |  |  |  | 5 |
| Breaking elongation | (%) | 417 | 490 | 510 | 460 | 463 | 443 |
| Yield point | (MPa) | 1.0 | 1.2 | 0.3 | — | — | 1.1 |
| Breaking strength | (MPa) | 18.6 | 20.9 | 10.6 | 32.8 | 25.6 | 20.3 |
| Tensile modulus | (MPa) | 30.4 | 21.6 | 7.8 | 37.6 | 25.8 | 27.1 |
| Permanent elongation | (%) | 5 | 10 | 10 | 15 | 15 | 10 |
| 100% modulus | (MPa) | 2.1 | 2.1 | 1.4 | 5.3 | 4.7 | 2.2 |
| 300% modulus | (MPa) | 5.1 | 4.3 | 2.8 | 13.7 | 10.5 | 4.8 |
| MFR | (200° C.) | 2.00 | 1.91 | 2.74 | 5.42 | 9.72 | 1.96 |
| Haze | (%) | 12.0 | 18.2 | 22.3 | 26.0 | 35.6 | 18.2 |
| Hardness | (Shore D) | 31 | 24 | 16 | 35 | 28 | 28 |
|  | (Shore A) | 82 | 68 | 59 | 89 | 85 | 81 |
| Tm | (° C.) | 14.1 | 2.4 | −0.0 | −14.2 | −25.4 | >8 |
|  |  | 40.9 | 18.3 | 12.2 | 2.0 | −6.5 | 19.1 |
| Vicat softening point | (° C.) | 47.3 | 45.8 |  |  |  | 47.5 |

TABLE 8-continued

|  |  | Example 36 | Example 37 | Example 38 | Example 39 | Example 40 | Example 41 |
|---|---|---|---|---|---|---|---|
| P-6 |  |  |  |  |  |  |  |
| P-7 |  |  |  |  |  |  |  |
| P-8 |  |  |  |  |  |  |  |
| CP-2 |  | 100 | 100 |  |  |  |  |
| CP-3 |  |  |  | 100 | 100 |  |  |
| CP-4 |  |  |  |  |  | 100 | 100 |
| EG8180 |  |  |  |  |  |  |  |
| NM-280 |  | 5 |  | 5 |  | 5 |  |
| PW-90 |  |  |  |  |  |  |  |
| PL-100 |  |  | 5 |  | 5 |  | 5 |
| DOP |  |  |  |  |  |  |  |
| Breaking elongation | (%) | 533 | 550 | 577 | 593 | 320 | 323 |
| Yield point | (MPa) | — | — | — | — | 0.6 | 1.7 |
| Breaking strength | (MPa) | 38.7 | 29.9 | 22.5 | 19.9 | 28.7 | 20.0 |
| Tensile modulus | (MPa) | 8.4 | 8.0 | 4.5 | 4.3 | 178.6 | 63.9 |
| Permanent elongation | (%) | 10 | 10 | 10 | 10 | 5 | 10 |
| 100% modulus | (MPa) | 3.0 | 3.1 | 2.1 | 2.1 | 3.5 | 4.6 |
| 300% modulus | (MPa) | 5.5 | 5.2 | 3.8 | 3.6 | 22.8 | 17.6 |
| MFR | (200° C.) | 1.07 | 0.69 | 2.34 | 2.29 | 3.93 | 3.13 |
| Haze | (%) | 58.4 | 32.0 | 89.0 | 79.5 | 25.4 | 31.5 |
| Hardness | (Shore D) | 28 | 27 | 24 | 22 | 57 | 46 |
|  | (Shore A) | 77 | 74 | 68 | 66 | 98 | 78 |
| Tm | (° C.) | −29.2 | −24.6 | −18.2 | −18.9 | 13.9 | 9.1 |
|  |  | 56.4 | 57.3 | 44.6 | 42.0 | 30.1 | 21.8 |
| Vicat softening point | (° C.) | 57.2 | 57.6 | 49.3 | 46.4 | 50.7 | 47.6 |

|  |  | Comp. Ex. 3 | Comp. Ex. 4 | Comp. Ex. 5 | Comp. Ex. 6 |
|---|---|---|---|---|---|
| P-6 |  |  |  |  |  |
| P-7 |  |  |  |  |  |
| P-8 |  |  |  |  |  |
| CP-2 |  |  |  |  |  |
| CP-3 |  |  |  |  |  |
| CP-4 |  |  |  |  |  |
| EG8180 |  | 100 | 100 | 100 | 100 |
| NM-280 |  | 5 |  |  |  |
| PW-90 |  |  | 5 |  |  |
| PL-100 |  |  |  | 5 |  |
| DOP |  |  |  |  | 5 |
| Breaking elongation | (%) | 977 | 943 | 943 | 900 |
| Yield point | (MPa) | — | — | — | — |
| Breaking strength | (MPa) | 16.6 | 16.6 | 18.3 | 17.6 |
| Tensile modulus | (MPa) | 7.5 | 6.8 | 6.3 | 6.0 |
| Permanent elongation | (%) | 10 | 10 | 10 | 10 |
| 100% modulus | (MPa) | 2.1 | 2.1 | 2.1 | 2.0 |
| 300% modulus | (MPa) | 3.0 | 3.0 | 3.0 | 2.9 |
| MFR | (200° C.) | 3.11 | 4.23 | 5.09 | 4.64 |
| Haze | (%) | 15.3 | 22.9 | 13.5 | 21.8 |
| Hardness | (Shore D) | 16 | 20 | 20 | 16 |
|  | (Shore A) | 60 | 71 | 63 | 56 |
| Tm | (° C.) | −60.9 | −60.6 | −59.0 | −68.5 |
|  |  | 59.0 | 59.25.8 | 60.6 | 41.7 |
| Vicat softening point | (° C.) | 55.7 | 55.8 | 55.4 | 55.5 |

TABLE 9

Changes in various physical property values after irradiation with γ-rays

| | | Example 44 | | Example 45 | | Example 46 | |
|---|---|---|---|---|---|---|---|
| | | Resin | | | | | |
| | | P-6 | | P-7 | | P-8 | |
| | | Before sterilization | After sterilization | Before sterilization | After sterilization | Before sterilization | After sterilization |
| Breaking elongation | (%) | 370 | 343 | 473 | 430 | 487 | 467 |
| Yield point | (MPa) | — | — | — | — | — | — |
| Breaking strength | (MPa) | 28.5 | 29.3 | 33.9 | 32.8 | 33.6 | 41.3 |
| Tensile modulus | (MPa) | 22.5 | 33.7 | 5.1 | 4.4 | 8.3 | 8.4 |
| Permanent elongation | (%) | 10 | 10 | 30 | 20 | 10 | 10 |
| 100% modulus | (MPa) | 2.6 | 3.6 | 1.8 | 2.5 | 3.0 | 3.3 |
| 300% modulus | (MPa) | 11.6 | 17.7 | 2.9 | 5.9 | 5.7 | 6.9 |
| MFR | (200° C.) | 0.76 | 0.46 | 1.35 | 0.70 | 1.00 | 0.41 |
| Hardness | (Shore D) | 60 | 58 | 21 | 24 | 27 | 29 |
| | (Shore A) | 98 | 99 | 71 | 73 | 78 | 78 |

| | | Comp. Ex. 7 | | Comp. Ex. 8 | |
|---|---|---|---|---|---|
| | | Resin | | | |
| | | PP | | PE | |
| | | Before sterilization | After sterilization | Before sterilization | After sterilization |
| Breaking elongation | (%) | 833 | 666 | 750 | 707 |
| Yield point | (MPa) | 33.7 | 34.4 | 9.0 | 9.2 |
| Breaking strength | (MPa) | 43.5 | 32.5 | 41.2 | 40.8 |
| Tensile modulus | (MPa) | 383.8 | 299.7 | 85.9 | 115.0 |
| Permanent elongation | (%) | 60 | 40 | 100 | 100 |
| 100% modulus | (MPa) | 19.5 | 20.8 | 9.0 | 9.1 |
| 300% modulus | (MPa) | 19.5 | 20.7 | 9.4 | 10.1 |
| MFR | (200° C.) | 5.87 | 29.76 | 7.14 | 1.61 |
| Hardness | (Shore D) | 74 | 76 | 48 | 51 |
| | (Shore A) | 99 | 100 | 97 | 98 |

PP: F-103 homopolypropylene (grand polypro)
PE: 1520L linear low density polyethylene (Mitsui Chemical)

TABLE 10

| | Catalyst | St content Mol % | Mw × $10^4$ | Mw/Mn mmol | Tacticity m-value *1 | λ-value |
|---|---|---|---|---|---|---|
| P-10 | A | 7 | 11.8 | 2.0 | >0.95 | 4 |
| P-11 | A | 56 | 16.0 | 1.9 | >0.95 | 57 |
| P-12 | A | 28 | 15.8 | 2.5 | >0.95 | 18 |

TABLE 11

| Resin constituent | D-1 | D-2 | D-3 | D-4 | D-5 |
|---|---|---|---|---|---|
| P-9 | 95 | 80 | 90 | | |
| P-10 | | | | 80 | |
| P-11 | | | | | 80 |
| DnDP | 5 | 20 | | | |
| BTHC | | | 10 | 20 | 20 |

DnDP: n-decyl phthalate
BTHC: tri-n-hexyl

TABLE 12

| | Example 47 | Example 48 | Example 49 | Example 50 | Example 51 | Control | Comp. Ex. 9 |
|---|---|---|---|---|---|---|---|
| Sheet layer construction and thickness | D-1 280 μm | P-9 10 μm<br>D-2 250 μm<br>P-9 20 μm | D-3 280 μm | P-10 10 μm<br>D-4 250 μm<br>P-10 20 μm | P-11 10 μm<br>D-5 250 μm<br>P-11 20 μm | PVC 280 μm | P-9 280 μm |
| Hemolysis level (mg/dl) | 43 | 45 | 42 | 49 | 46 | 44 | 247 |

Industrial Applicability

The medical material and the medical device comprising the aromatic vinyl compound/α-olefin random copolymer according to the present invention, are materials containing substantially no chlorine and have not only excellent flexibility, transparency and proper resiliency but also radiation resistance and biocompatibility, and they are hence especially useful in the medical field. They are suitable as medical devices and containers, such as medical tubes, medical catheters, blood bags, infusion solution bags, dialysis bags, artificial blood vessels, circuits, syringes, blood dialysers, blood component separators and artificial lungs, which are used in contact with the body fluid.

What is claimed is:

1. A medical device made out of a material comprising an aromatic vinyl compound/α-olefin random copolymer, which material has been sterilized to a degree suitable for medical application, wherein said material is obtained by processing a resin composition (C) obtained by blending 100 parts by weight of a resin component (A) containing at least 50 wt % of the aromatic vinyl compound/α-olefin random copolymer, and from 0.1 to 200 parts by weight of a plasticizer (B).

2. The medical device according to claim 1, wherein the medical device is selected from the group consisting of (a) intravascular insertion catheters, indwelling catheters, cerebrovascular treating catheters, thermodilution catheters, IVH catheters, indwelling needles, directers, stylettes, introducers and guide wires for said catheters; (b) balloons and balloon catheters; (c) catheters that are orally or nasally, insertable or retainable in digestive organs; (d) oxygen catheters, oxygen cannulas, tubes and cups adapted for endotracheal tubes, tubes and cups adapted for tracheotomy tubes, and endotracheal suction catheters; (e) catheters insertable or retainable in body cavities or systems; (f) endoscopic tubes; (g) stents, artificial blood vessels, artificial trachea, artificial bronchial tubes and artificial anus; (h) artificial lungs, artificial hearts, artificial kidneys, reservoirs, bubble traps, drip chambers, and hearts to constitute extracorporeal circuits; (i) blood bags, infusion solution bags, injection liquid bags, waste liquid bags, and parts connectable to said bags; (j) inspection instruments and treatment instruments required to have low friction resistance during retention in bodies or during sliding, and inspection instruments and treatment instruments which are required to have antithrombotic properties; (k) gas supply tubes and liquid supply tubes; and (l) contact lenses.

3. The medical device according to claim 1, wherein the aromatic vinyl compound/α-olefin random copolymer is such a copolymer produced by means of a catalyst comprising a transition metal compound for polymerization represented by the following formula and a co-catalyst:

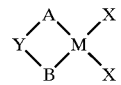

wherein A and B are groups selected from an unsubstituted or substituted cyclopentaphenanthryl group, an unsubstituted or substituted benzindenyl group, an unsubstituted or substituted cyclopentadienyl group, an unsubstituted or substituted indenyl group, or an unsubstituted or substituted fluorenyl group, provided at least one of A and B is an unsubstituted or substituted cyclopentaphenanthryl group, an unsubstituted or substituted benzindenyl group, or an unsubstituted or substituted indenyl group;

when each of A and B is an unsubstituted or substituted cyclopentaphenanthryl group, an unsubstituted or substituted benzindenyl group, or an unsubstituted or substituted indenyl group, the structures of the two may be the same or different;

Y is a methylene group, a silylene group or an ethylene group, which has bonds to A and B and which further has hydrogen or a $C_{1-15}$ hydrocarbon group, the substituents may be the same or different from one another, and Y may have a cyclic structure;

X is hydrogen, halogen, a $C_{1-15}$ alkyl group, a $C_{6-10}$ aryl group, a $C_{8-12}$ alkylaryl group, a silyl group having a $C_{1-4}$ hydrocarbon substituent, a $C_{1-10}$ alkoxy group, or a diarylamide group having a $C_{1-6}$ alkyl substituent; and M is zirconium, hafnium or titanium.

4. The medical device according to claim 1, which is a tube, a catheter, a circuit, a blood bag, an infusion solution bag or a dialysis bag, having antithrombogenicity imparted to its wetted surface.

5. A medical device made out of a material comprising an aromatic vinyl compound/α-olefin random copolymer, which material has been sterilized to a degree suitable for medical application, wherein antifogging properties are imparted by addition of an antifogging agent.

6. The medical device according to claim 1, which has a transparency such that the haze value as measured in a 1 mm thickness is not higher than 20%.

7. The medical device according to claim 1, wherein a resin other than the aromatic vinyl compound/α-olefin random copolymer contained in the resin composition (C) is at least one member selected from the group consisting of an olefin-containing resin and a styrene-containing resin.

8. In a method of performing a medical procedure using a medical device, the improvement comprising using a medical device made out of a material comprising an aromatic vinyl compound/α-olefin random copolymer, wherein said material is obtained by processing a resin composition (C) obtained by blending 100 parts by weight of a resin component (A) containing at least 50 wt % of the aromatic vinyl compound/α-olefin random copolymer, and from 0.1 to 200 parts by weight of a plasticizer (B).

* * * * *

UNITED STATES PATENT AND TRADEMARK OFFICE
CERTIFICATE OF CORRECTION

PATENT NO. : 6,630,215 B1
DATED : October 7, 2003
INVENTOR(S) : Oda et al.

It is certified that error appears in the above-identified patent and that said Letters Patent is hereby corrected as shown below:

<u>Title page, Item [54] and Column 1, line 1,</u>
Should read: -- [54] MEDICAL MATERIAL AND MEDICAL SUPPLY --

Signed and Sealed this

Sixth Day of January, 2004

JAMES E. ROGAN
*Director of the United States Patent and Trademark Office*